United States Patent [19]

Kifferstein et al.

[11] 4,070,027
[45] Jan. 24, 1978

[54] LIMB STIFFENING DEVICE

[76] Inventors: Harry P. Kifferstein, 27250 Harvard Road, Southfield, Mich. 48076; Warren M. Kifferstein, 29632 Middlebelt, Farmington Hills, Mich. 48024

[21] Appl. No.: 706,627

[22] Filed: July 19, 1976

[51] Int. Cl.² .......................... A63B 69/36; A61F 3/00
[52] U.S. Cl. .................................. 273/189 A; 128/90; 128/87 R; 46/DIG. 1
[58] Field of Search ........................ 273/189 R, 189 A; 128/77, 80 C, 89 R, 90, 87 R

[56] References Cited
U.S. PATENT DOCUMENTS

| | | | |
|---|---|---|---|
| 1,250,818 | 12/1917 | Dutard | 128/89 R |
| 2,671,444 | 3/1954 | Pease | 128/90 X |
| 3,074,723 | 1/1963 | Esty | 273/189 A |
| 3,799,158 | 3/1974 | Gardner | 128/80 C |
| 3,877,426 | 4/1975 | Nirschl | 273/189 R X |
| 3,990,709 | 11/1976 | De Rogatis | 273/189 A |

OTHER PUBLICATIONS

"The American Journal of Surgery", American Journal of Surgery, Inc., New York, Sept. 1945, pp. 299–305.

Primary Examiner—George J. Marlo
Attorney, Agent, or Firm—Hauke & Patalidis

[57] ABSTRACT

A limb stiffening device made of a length of tough, pliable and flexible material, preferably plastic, of open lattice pattern, having a continuous edge with radiused corners. The edge and the webs defining the open lattice pattern are substantially curvilinear in cross section. Fasteners are attached at opposite ends of the length of material for holding the length of material wrapped in the form of a sleeve around a limb, with the ends overlapped. The material is preferably provided with a preset bow tending to curl the length of material for facilitating wrapping around a limb, especially when a single hand is used for placing or removing the stiffening device, for example about the elbow of a golfer for preventing the golfer from bending his arm at the elbow while hitting a ball with a golf club.

7 Claims, 5 Drawing Figures

LIMB STIFFENING DEVICE

BACKGROUND OF THE INVENTION

The present invention relates to a limb stiffening device, and more particularly to a golfer aid which is wrapped around the golfer's elbow for preventing or limiting the amount of elbow bending for producing a longer range and more accurate tee and fairway golf shot.

It is very common for a golfer to develop an improper swing which causes his driven golf ball to hook or slice rather than take flight in a straight line, or which prevents the ball from being hit squarely with appropriate strength to provide a shot reaching an appreciable distance.

Poor distance reach, and hooking or topping the ball, which are common faults of novice and average golfers, are often the results of unconsciously developing a serious defect in drive techniques due to following the natural urge to flex the leading arm at the elbow, either just prior to impact with the ball or at the moment of impact. Such defective drive technique results in slicing or topping the ball and in a weak drive power causing both lack of directional precision and insufficient reach, thus requiring additional strokes to reach the greens. If elbow flexure of the leading arm is avoided, the results achieved are improvement of distance and direction aptitude, with the accompanying improvement of reducing the number of strokes necessary to reach a particular green and enabling the golfer to better control his game by insuring him of constantly repetitive drives and shots.

The present invention provides a removable and adjustable arm stiffener normally worn about the middle portion, i.e., at the elbow portion, of a golfer's arm, which prevents the golfer's leading arm from collapsing at the elbow by providing a stiffening force increasing as a function of the amount of elbow bending, while swinging for hitting a tee shot, a fairway shot, or even during putting. By forcing the golfer to straighten his leading arm and to keep it straight throughout the complete shot, a longer swinging arc is obtained, thus causing the golf club head to travel faster at impact with the ball, while preventing topping or slicing of the ball. Consequently, much longer and straighter golf shots result, and such results are achieved shot after shot such that the golfer is rapidly taught to develop a "groove."

Golfer arm stiffening devices have been designed in the past. For example, one U.S. Letters Patent, discloses a removable cuff or sleeve disposed about the elbow of the leading arm of a golfer and provided about the crook of the elbow with longitudinal pockets in which are removably fitted spring metal strips such as to tailor the amount of stiffening of the elbow joint according to the stiffness or number of spring metal strips disposed in the pockets. The cuff is held in position by means of straps and buckles. Such a device is difficult to place upon the arm with one hand, is not comfortable to wear as interfering with blood circulation and preventing the skin from perspiring, and it is heavy and combersome.

Another U.S. Letters Patent discloses an inflatable ribbed cuff placed about the elbow of a golfer's leading arm. The amount of stiffness of the cuff is a function of the pressure of inflation of the cuff. Such a stiffening device requires that several sizes be made for accomodating arms of different circumferences, and they are uncomfortable to wear, especially in hot weather as they must be made of rubber-like imperforate material. In addition, they require to be passed over the hand and wrist and pulled to about the elbow, being held manually there while the user mouth-inflates the cuff, and the projecting air valve may cause injury or at least discomfort. They cannot be deflated, when over-inflated, with any degree of precision to provide a desired stiffness, without many try-outs and successive partial inflations and deflations until the desired amount of stiffness is obtained.

The present invention, by contrast, provides an arm stiffener which may be worn either about the left or right elbow, either directly on the skin or over clothing. It can be easily placed in position with one hand, and taken off at will, without any fuss. It can be worn at all times, or put on and removed as many times as the user desires. The amount of stiffening of the arm can be easily adjusted. The open mesh, or open pattern, of the stiffening device of the invention allows for variable flexibility at the outside elbow bone, while the overlap of material at the crook of the elbow, by providing a double thickness of material, tends to keep the elbow as straight and as taut as desired. The open lattice design of the arm straightener of the invention allows perspiration to be effected in a normal manner, such that it may be worn at all times if so desired. The open lattice design further permits to obtain an arm stiffener which is light in weight, and therefore does not interfere with the normal swinging motion of a golfer addressing the ball. Furthermore, the open lattice design permits to strategically place soft resilient material cushions at appropriate locations, and more particularly at the location of the protruding elbow bone. The cushions are removable, such that the straightening device of the invention may be used with or without the cushions, and the cushions located at any appropriate position.

The present invention can also be used as a surgical appliance for setting and immobilizing broken bones in the arm or leg or, alternatively, for stiffening and momentarily immobilizing damaged joints, such as the wrist, the elbow or the knee, while healing.

SUMMARY OF THE INVENTION

The present invention accomplishes its object by providing a limb stiffening device consisting of a relatively stiff, but pliable and relatively flexible flat piece of open web or open lattice material, such as plastic and the like, provided with fastening means proximate each end, which is normally worn wrapped about a limb portion, with the fastening means adjustably mutually engaged. The open lattice structure results in light weight and permits aeration of the surface covered by the device. The fastening means are preferably of the type consisting of textile material possessing mutually engaging characteristics.

Other objects and advantages of the present invention will be apparent to those skilled in the art when the following description of the best mode contemplated for practicing the invention is read in conjunction with the accompanying drawing wherein:

DETAILED DESCRIPTION OF THE PREFERRED EMBODIMENT

Figure 1:
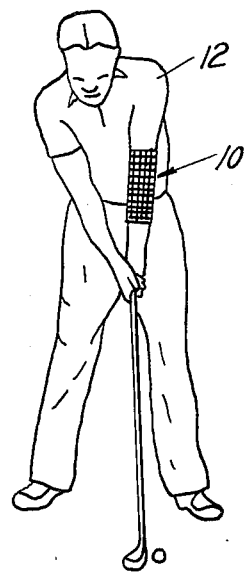
FIG. 1 is a front elevation view of a person, such as a golfer, showing the limb stiffening device of the invention attached to the person's arm.
Figure 2:
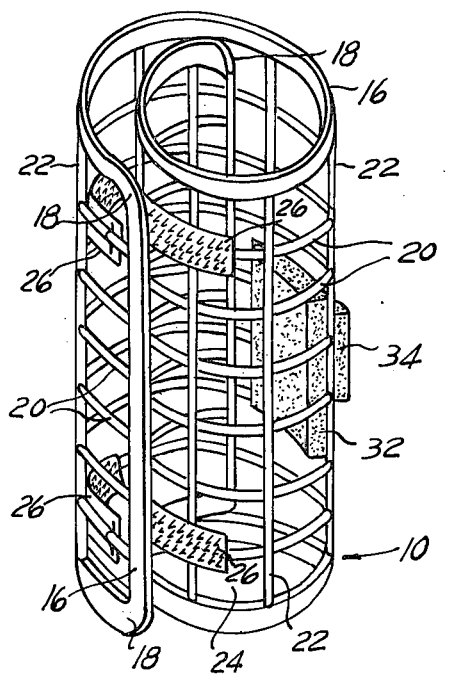
FIG. 2 is a perspective view of the limb stiffening device of the invention.
Figure 3:
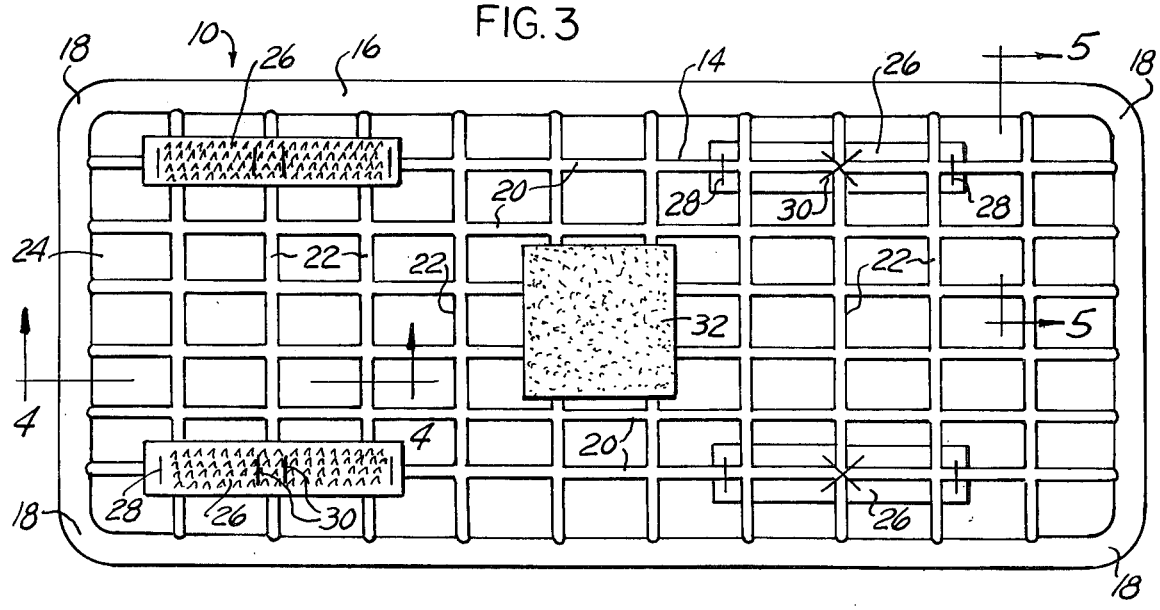
FIG. 3 is a plane view of the device in an unwrapped and flat condition.
Figure 4:
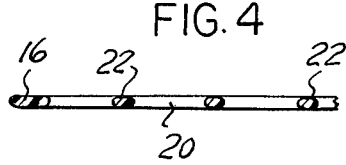
FIGS. 4 and 5 are sectional views respectively along lines 4—4 and 5—5 of FIG. 3.
Figure 5:
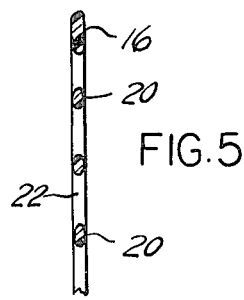

As shown at FIG. 1, the limb stiffening device 10 of the invention, when used as a golfer's aid, is worn about the elbow and crook of the left arm 12, or leading arm, of a golfer, assuming a right-handed golfer. A left-handed golfer would, of course, wear the limb stiffening device 10 on his right arm. As best shown at FIGS. 2 and 3, the limb stiffening device 10 is made of a length of open lattice material, or framework, 14 generally rectangular in its flattened condition illustrated at FIG. 3, and provided with a reinforced edge web 16, having radiused corners 18. The open lattice material 14 has a plurality of substantially parallel web members 20, substantially parallel to each other and parallel to the lengthwise edge of the generally rectangular framework 14, and a plurality of parallel webs 22 disposed substantially parallel to the shorter sides of the generally rectangular framework 14. Preferably, the limb stiffening device framework 14 is molded of an appropriate flexible material, such as a plastic and, as best shown at FIGS. 4 and 5, its web members 20 and 22 have a curvilinear cross section. The edge web portion 16 is also provided with a curvilinear cross section, and, although it has about the same thickness than the web members 20 and 22, it is preferably wider, as illustrated, although it may be of the same width.

Although the web members 20 and 22 have been illustrated as being disposed at right angles to each other and respectively parallel to the lengthwise portion of the edge 16 and to the shorter portion of the edge 16, it will be readily apparent that the open lattice rectangular pattern may be of a different design, such as a lozange, hexagonal, octagonal, square or triangular lattice design, or it may consist of a continuous sheet of material with a multitude of rectangular, square or round apertures, instead of forming the rectangular apertures 24 illustrated or, in the alternative, the web members 20 and 22 may be disposed non-parallel to the edges of the framework 14. Depending on the local pressure and tension desired, a diversity of lattice pattern shapes may be used in a single framework.

Proximate each end of the framework 14, there is a length of textile material 26 possessing mutually engaging characteristics, such as the textile material known and sold under the trademark Velcro, which is fastened to the webs 20 and 22 such, for example by means of straight stitches 28 and cross stitches 30. A pair of such pieces or lengths of textile material 26, each rectangular in shape, are shown affixed to the framework 14 proximate one end thereof facing in one direction, and another pair of similar textile material 26 is shown fastened to the framework 14 proximate the other end thereof facing in an opposite direction. Other fastening means may be used, such as clips, buckles, hooks and the like, but the most convenient fastening means as far as ease of manipulation and precision of size adjustment consists of the means illustrated and described.

In this manner, when the framework 14 is wrapped around a limb, such as an arm elbow and elbow crook, the length of the framework 14 is such as to permit overlap of the two ends thereof with the mutually engaging textile pieces 26 mutually presenting their effective surfaces. Preferably, especially when the limb straightening device of the invention is used as a golfer aid, the overlapping end portions are placed at the crook of the elbow so as to position a double thickness of material at the crook which increases the stiffening effect of the wrapped sleeve formed by the stiffening device 10. Preferably, the framework 14 is given a preset built-in bow or self-curling tendency, generally as shown in the perspective view of FIG. 2, such that very little effort is required to wrap it around a limb such as an arm, and that the wrapper may be tightened about the arm with any degree of tightness, with a single hand, by holding one end of the framework 14 with some fingers, and using other fingers, such as the thumb, passed in an appropriate aperture 24 to exercise a pulling action on the other end of the framework 14.

Because of the double thickness of material at the crook of the elbow, as previously mentioned, stiffness of the wrapped limb stiffening device 10 is concentrated on the inside of the elbow joint. However, because of the single thickness of material where engaged with the tip of the elbow, and because of the relative resiliency of the material when pressure is exerted on a short length of the ribs 20 and 22, there is very little interference with the protruding elbow bone. If desired a small cushion 32, FIGS. 2 and 3, of soft resilient material such as sponge rubber or rubber-like plastic may be attached to the framework 14 at a location corresponding to the tip of the elbow, to afford additional protection, as illustrated. The cushion 32 is provided with a projecting portion or knob 34, of overall dimension larger than the apertures 24, which is passed through one of such apertures 24 to hold the cushion 32 in position. Also, if so desired, a plurality of such cushions 32 may be disposed at appropriate locations.

Because of the lattice framework construction adapted, the limb stiffening device 10 of the invention is very light in weight, and provides adequate aeration through the apertures 24. In addition, because every corner 18 of the continuous reinforced web 16 is radiused and the edge rib 16 together with the framework ribs 20 and 22 are curvilinear in section, there is very little danger of sharp corners gouging or scuffing the skin of the wearer.

It will be readily apparent that when worn about the elbow joint, as shown at FIG. 1, the limb stiffening device of the invention is of great help to a golfer in forcing him to keep his leading arm straight when addressing the ball. It will also be readily apparent to those skilled in the art that the limb stiffening device of the invention may be used as a surgical appliance for restraining and stiffening limbs having broken bones or damaged joints. Although the framework 14 has been illustrated and described as being substantially rectangular in shape, it will be readily apparent that it may take any other appropriate shape, such as trapezoidal, hexagonal, octagonal, square, circular, oval, or the like, and that instead of being flat when unfolded, as shown at FIG. 3, it may be provided with a built-in taper, or bulges, or shaped as desired to better conform to a limb shape. Because of the readily adjustable fastening means adopted for fastening the ends of the framework, one or two sizes, at the most, are sufficient to provide a wide range of arm circumferences when the invention is used as an elbow straightener golfing aid.

For some applications of the limb stiffening device of the invention it may be found desirable to provide fastening means, such as clips, for example, permitting the framework ends to be attached together in an abutting fashion.

Having thus described the invention by way of an example of practical embodiment thereof, variations whereof will be apparent to those skilled in the art, what is claimed as new is as follows:

1. A stiffening device for a limb joint comprising a single length of tough flexible non-elastic material of open lattice pattern having a continuous edge provided with radiused corners, said open lattice pattern having a plurality of integral web members extending from edge to edge in criss-cross arrangement, each of said web members and said edge being substantially curvilinear in cross section, and means for attaching opposite ends of said length of material in overlapped fashion when wrapped around a limb joint, wherein the overlapped ends of said length of material are disposed at the crook of said limb joint and said length of material is formed with a bow causing said material to tend to curl upon itself lengthwise and about said limb.

2. The device of claim 1 wherein said web members form a rectangular lattice pattern.

3. The device of claim 2 wherein said web members are disposed in a pair of groups of parallel rows each substantially parallel to a pair of parallel edges of said length of material.

4. The device of claim 1 wherein said means for attaching opposite ends of said length of material comprise at least one piece of textile material possessing mutually engaging characteristics fastened proximate each end of said length of material for mutual releasable engagement of said overlapped ends.

5. The device of claim 1 wherein said material is a plastic material.

6. The device of claim 1 further comprising at least one cushion of soft resilient material disposed at a predetermined location on a surface of said length of material.

7. The device of claim 6 wherein said cushion is removably fastened to said lattice pattern by being provided with a resilient knob of overall dimensions larger than the apertures in said lattice pattern projecting through one of said apertures.

* * * * *